(12) United States Patent
Kim et al.

(10) Patent No.: US 10,787,607 B2
(45) Date of Patent: *Sep. 29, 2020

(54) HIGH EFFICIENCY FLUORESCENT COMPOUND AND METHOD FOR PREPARING THE SAME

(75) Inventors: Seong Keun Kim, Seoul (KR); Seung Bum Park, Seoul (KR); Il Seung Yang, II, Seoul (KR); Eun Ha Kim, Seoul (KR); Jun Hee Kang, Seoul (KR)

(73) Assignee: SNU R&DB FOUNDATION, Seoul (KR)

( * ) Notice: Subject to any disclaimer, the term of this patent is extended or adjusted under 35 U.S.C. 154(b) by 823 days.

This patent is subject to a terminal disclaimer.

(21) Appl. No.: 14/344,585

(22) PCT Filed: Sep. 5, 2012

(86) PCT No.: PCT/KR2012/007133
§ 371 (c)(1),
(2), (4) Date: Jun. 11, 2015

(87) PCT Pub. No.: WO2013/039307
PCT Pub. Date: Mar. 21, 2013

(65) Prior Publication Data
US 2019/0330524 A1   Oct. 31, 2019

(30) Foreign Application Priority Data

Sep. 16, 2011 (KR) .......................... 10-2011-0093191
Jul. 30, 2012 (KR) .......................... 10-2012-0083374

(51) Int. Cl.
| C07C 49/00 | (2006.01) |
| C09K 11/00 | (2006.01) |
| H01L 51/00 | (2006.01) |
| C09K 11/06 | (2006.01) |
| C07C 49/248 | (2006.01) |
| C07C 49/255 | (2006.01) |
| C07H 15/203 | (2006.01) |
| A61K 49/00 | (2006.01) |
| A61N 5/06 | (2006.01) |
| H01L 51/50 | (2006.01) |

(52) U.S. Cl.
CPC .......... C09K 11/06 (2013.01); A61K 49/0021 (2013.01); A61K 49/0052 (2013.01); A61K 49/0054 (2013.01); A61N 5/062 (2013.01); C07C 49/248 (2013.01); C07C 49/255 (2013.01); C07H 15/203 (2013.01); H01L 51/0052 (2013.01); H01L 51/5012 (2013.01); C09K 2211/1011 (2013.01)

(58) Field of Classification Search
CPC .... C07C 49/248; C09K 11/06; H01L 51/0052
See application file for complete search history.

(56) References Cited

U.S. PATENT DOCUMENTS

2010/0081724 A1   4/2010   Souto
2015/0031867 A1   1/2015   Kim et al.

FOREIGN PATENT DOCUMENTS

| KR | 10-2009-0041632 | 4/2009 |
| KR | 10-2013-0030326 A | 3/2013 |
| KR | 10-1244176 B1 | 3/2013 |
| KR | 10-1294993 B1 | 8/2013 |
| WO | 2009/054608 | 4/2009 |
| WO | 2013/039307 A2 | 3/2013 |
| WO | 2013039308 A2 | 3/2013 |

OTHER PUBLICATIONS

Yang, et al., "Photochemical Generation of a New, Highly Fluorescent Compound from Non-Fluorescent Resveratrol", Chemical Communications, (Feb. 24, 2012) pp. 3839-3841.
International Search Report—PCT/US2012/007137—ISA/KR—dated Feb. 28, 2013 (dated Feb. 28, 2013).
Written Opinion—PCT/US2012/007137—ISA/KR—dated Feb. 28, 2013 (dated Feb. 28, 2013).
Kim, H. M. et al. "Two-Photon Fluorescent Turn-On Probe for Lipid Rafts in Live Cell and Tissue" Journal of the American Chemical Society (2008), 130(13), 4246-4247.
Lemhadri, M. et al. "Palladium-Catalyzed Heck Reasctions of alk-1-en-3-ones with Aryl Bromides: A Very Simple Access to (E)-1-arylalk-1-en-3-one", Synthesis 2009. pp. 1021-1035, 15 Pages.
Written Opinion issued by the International Searching Authority for PCT/KR2012/007133 dated Feb. 28, 2013. 5 pages.
Search Report issued by the International Searching Authority for PCT/KR2012/007133 dated Feb. 28, 2013. 3 pages.
Korean Office Action, Issued by the Korean Intellectual Property Office, dated Mar. 19, 2013, for Korean Application No. 2012-0083374. 4 Pages.

*Primary Examiner* — Sikarl A Witherspoon
(74) *Attorney, Agent, or Firm* — Brundidge & Stanger, P.C.

(57) ABSTRACT

The present invention provides a fluorescent resveratrone [(E)-4-(6,8-dihydroxynaphthalen-2-yl)but-3-en-2-one] and its derivatives having Formula 1 and a method for preparing the same by a photochemical reaction of resveratrol and its derivatives which are not fluorescent having Formula 7 or Formula 8. The new fluorescent compounds of the present invention has single-photon absorptive characteristics and/or two-photon absorptive characteristics as well as no or little toxicity according to a cytotoxicity test and can be usefully utilized in the field of organic fluorescent element, display element, spectrometer, two-photon absorptive storing device, laser micro processing apparatus, photo dynamic therapy apparatus and the like.

13 Claims, 10 Drawing Sheets

[Fig. 1]
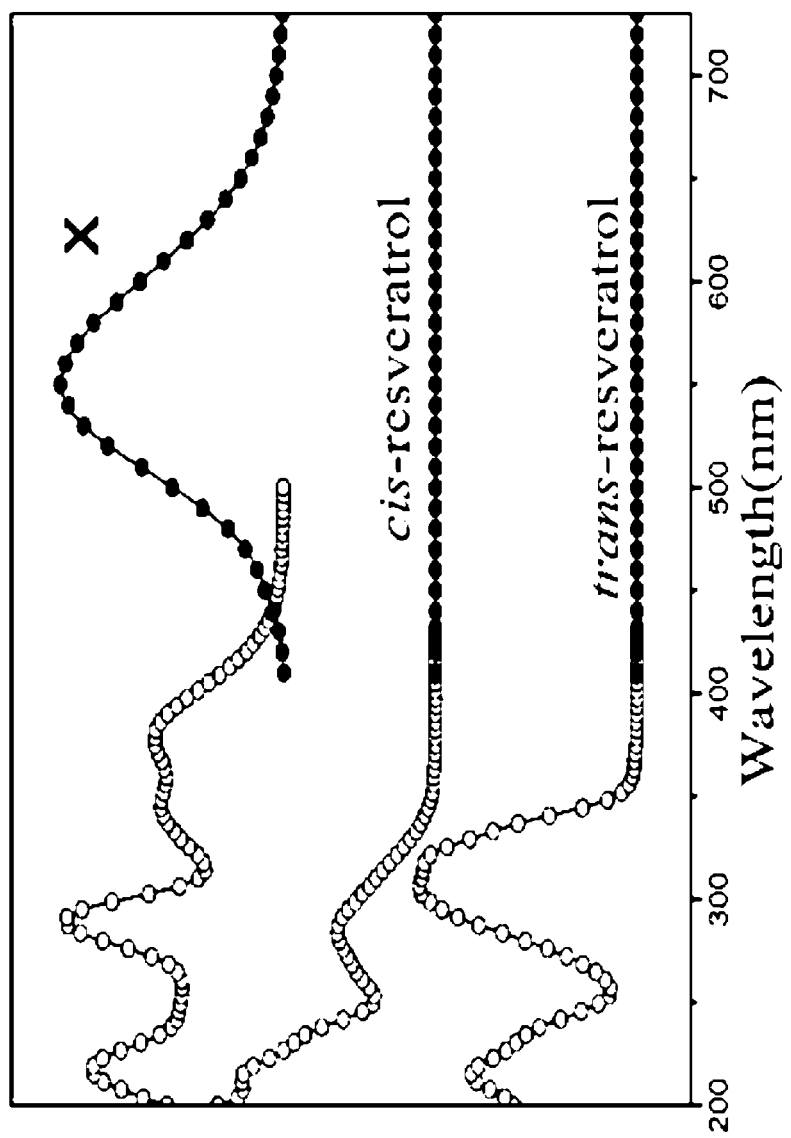

[Fig. 2]
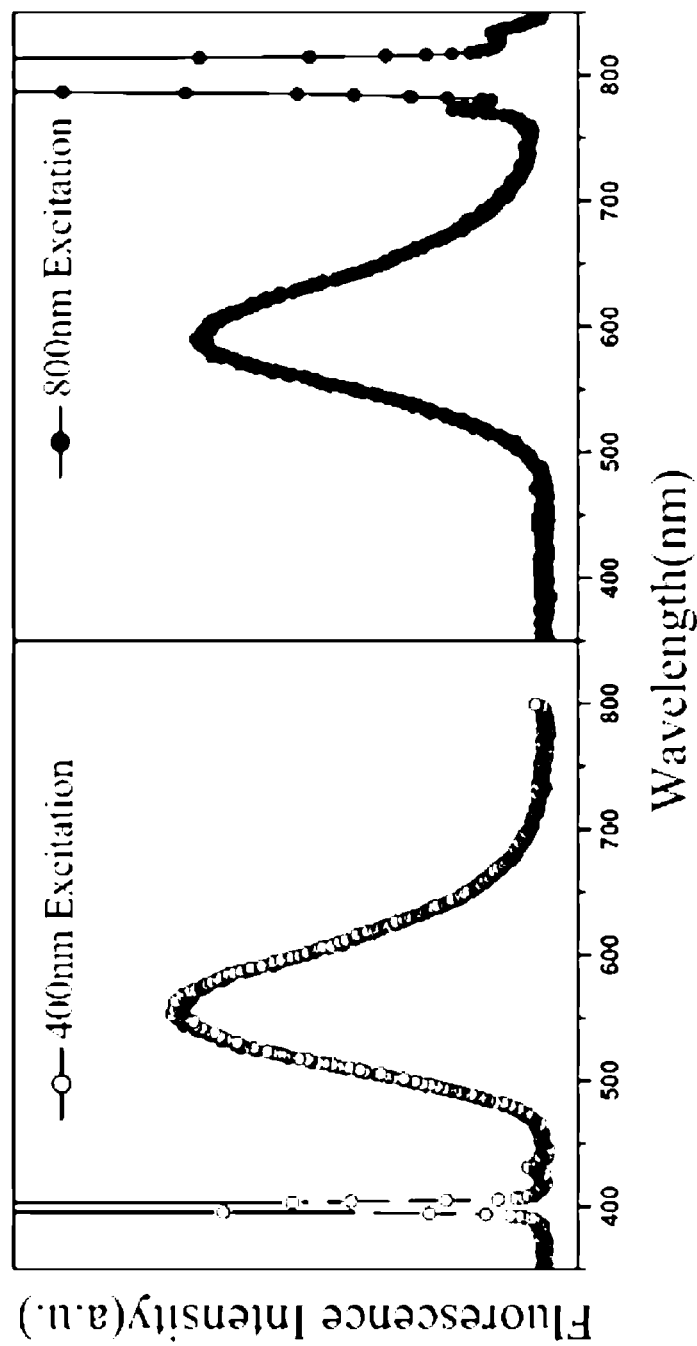

[Fig. 3]
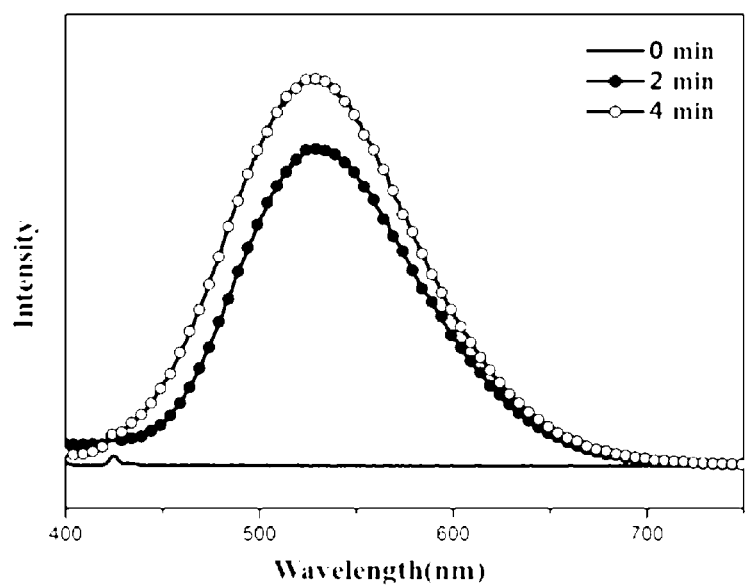
[Fig. 4]
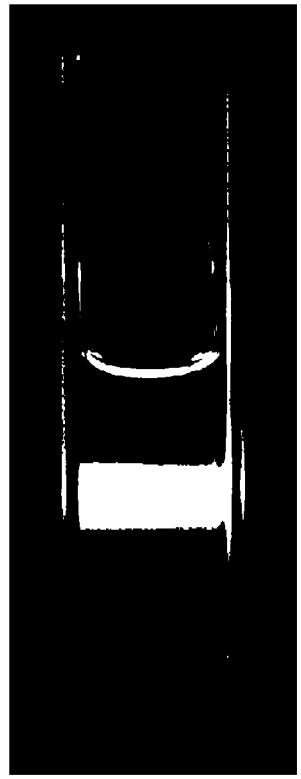

[Fig. 5]
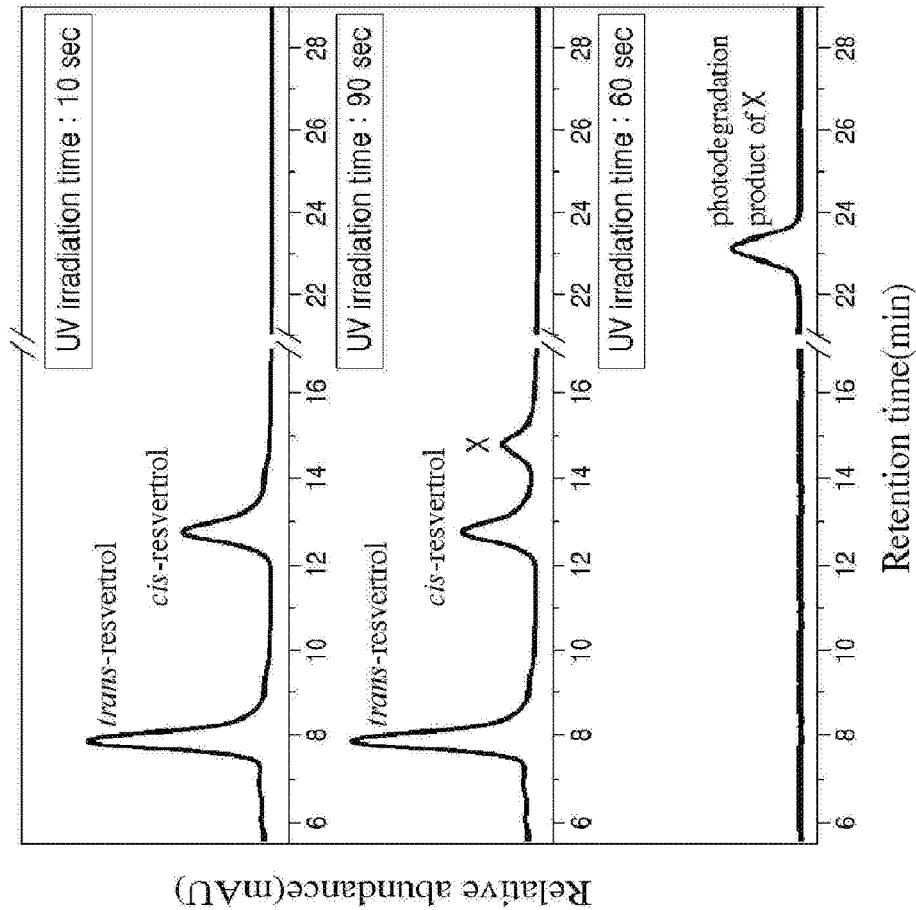
[Fig. 6]
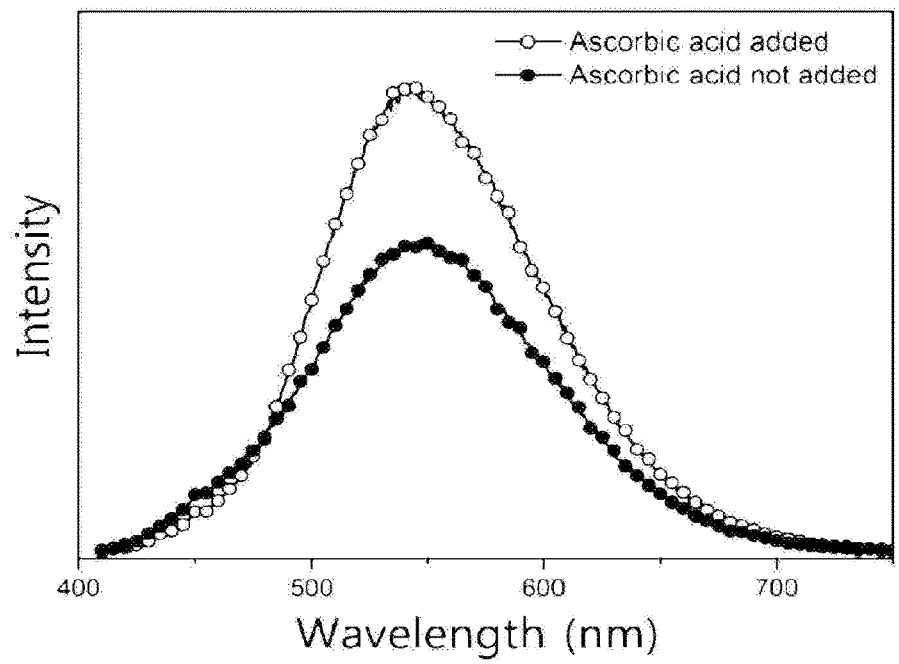

[Fig. 7]
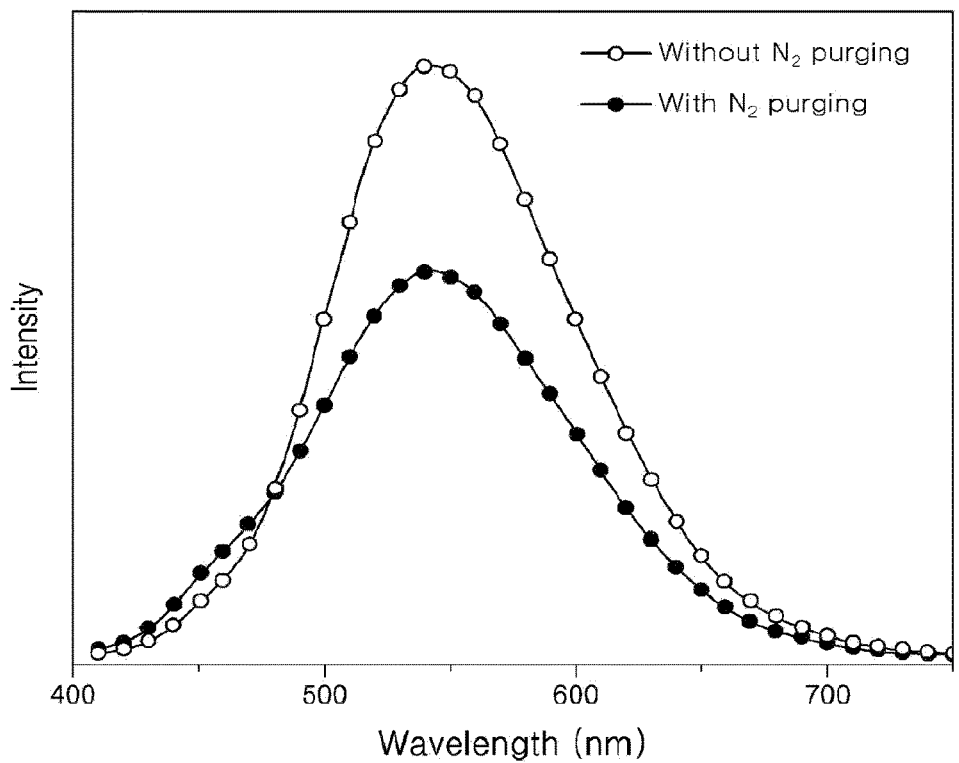
[Fig. 8]
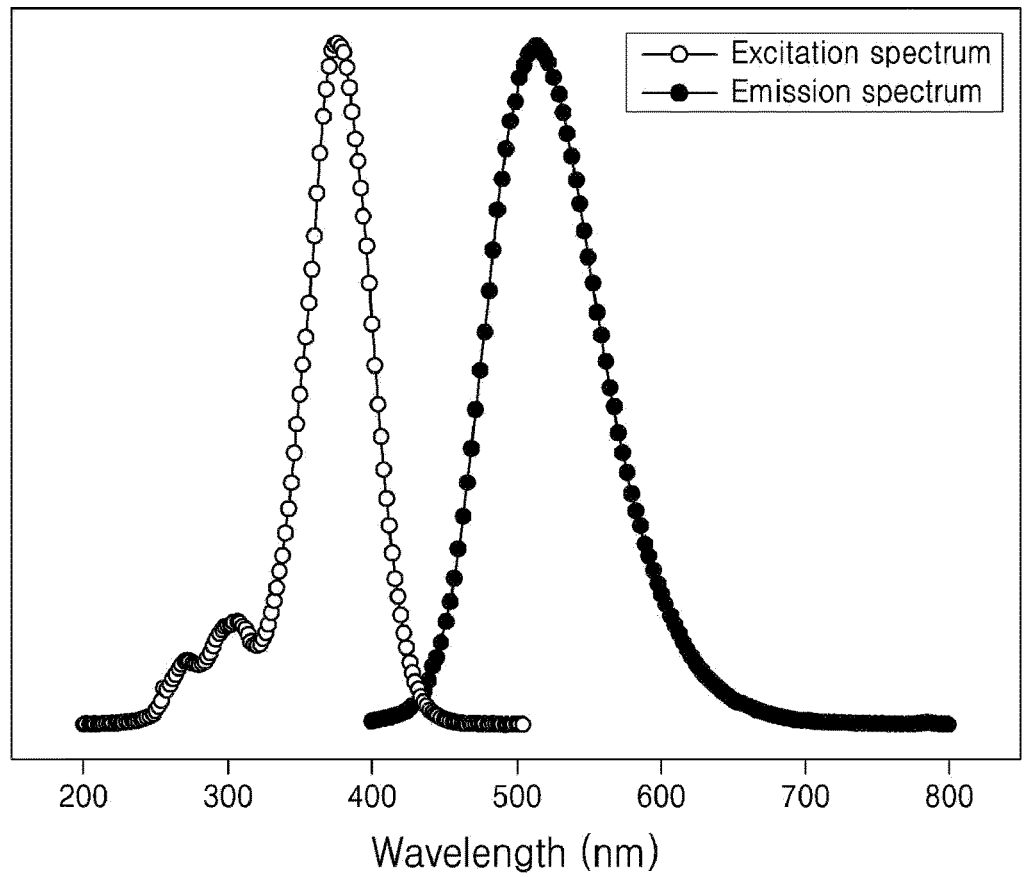

[Fig. 9]
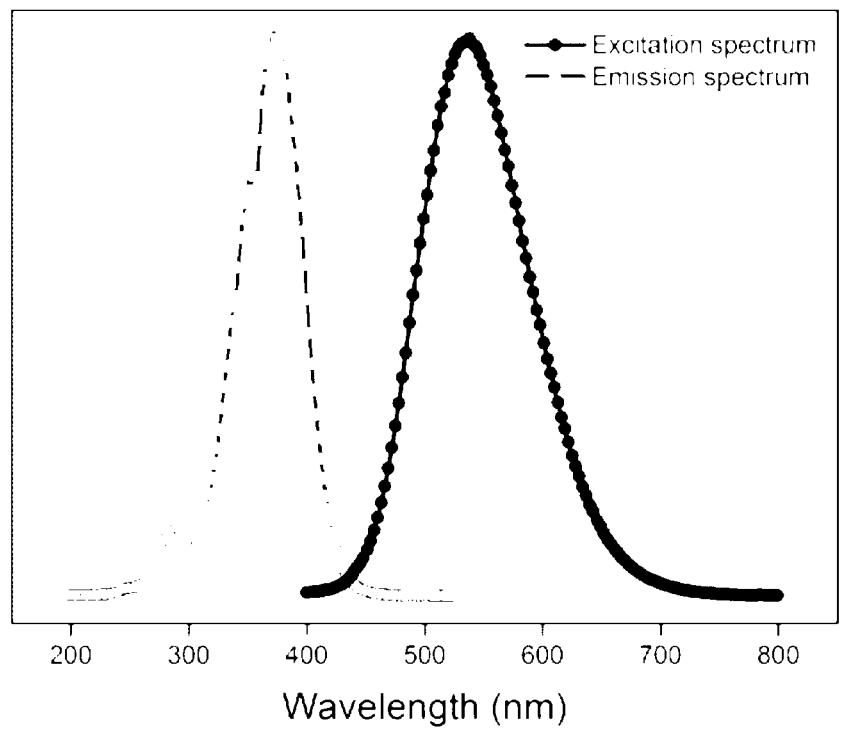
[Fig. 10]
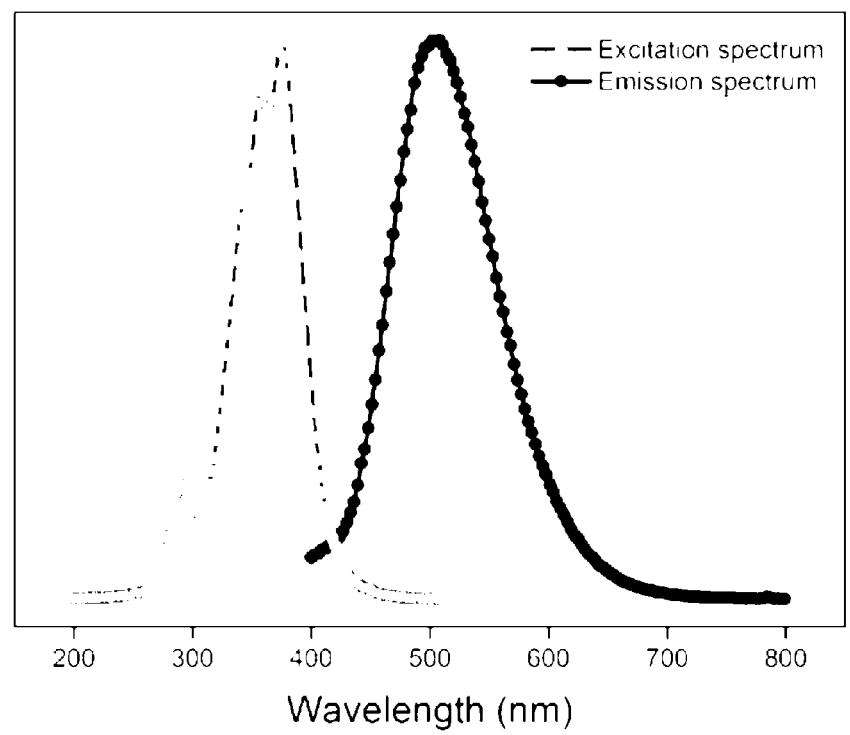

[Fig. 11]
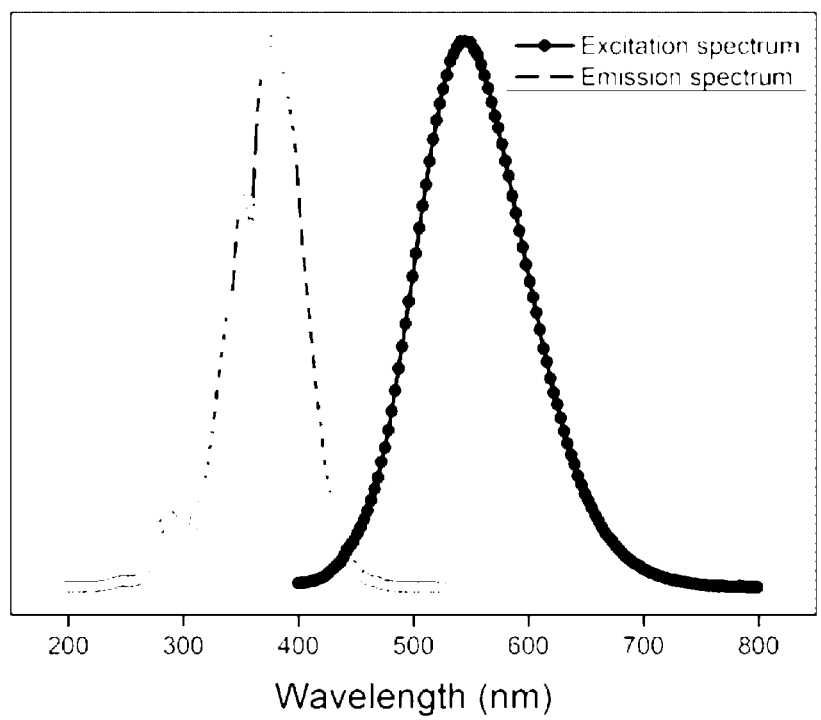

[Fig. 12]
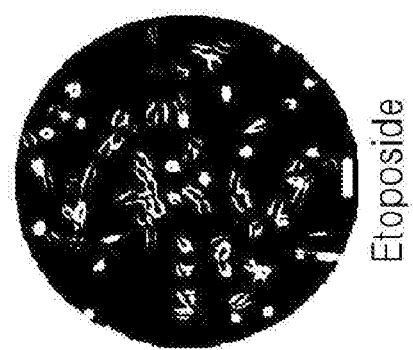
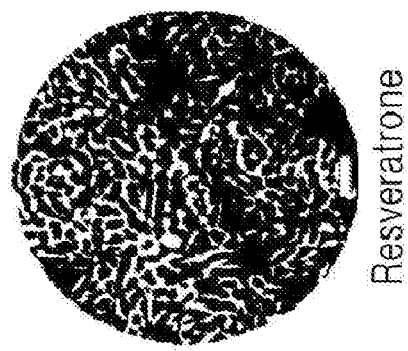
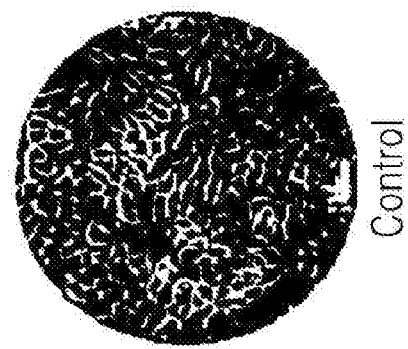

[Fig. 13]
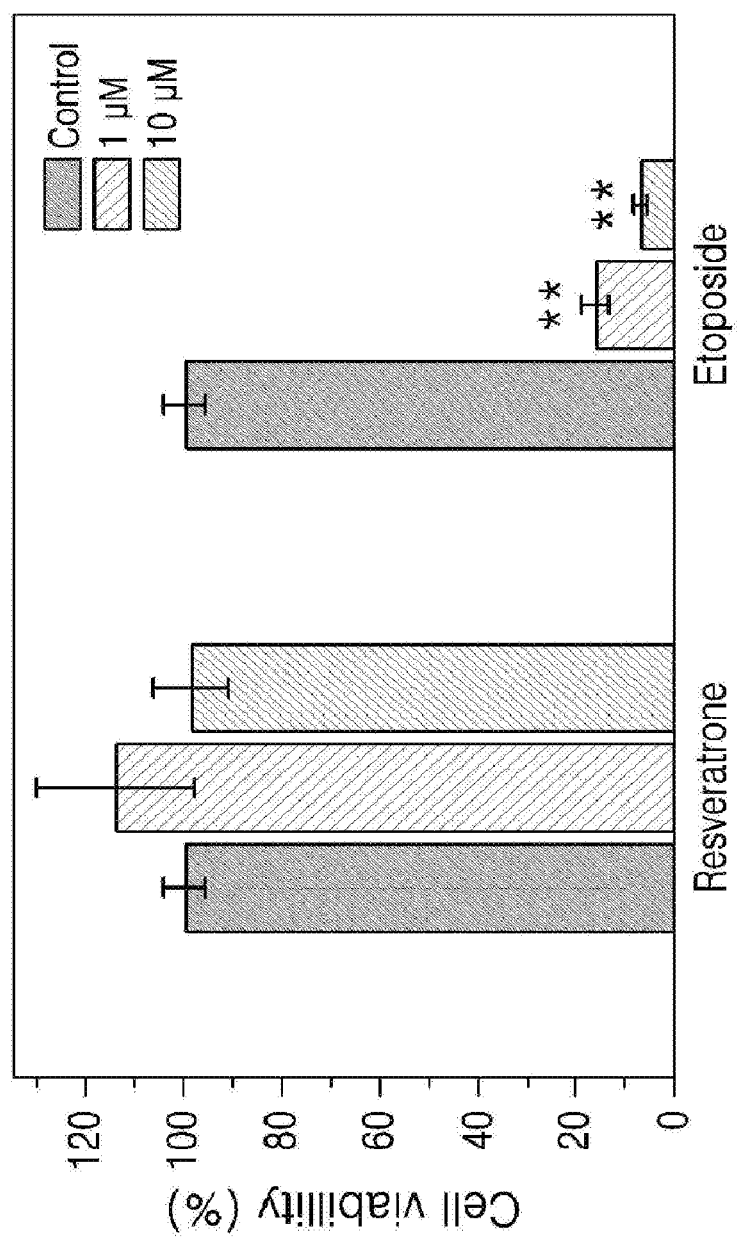

[Fig. 14]
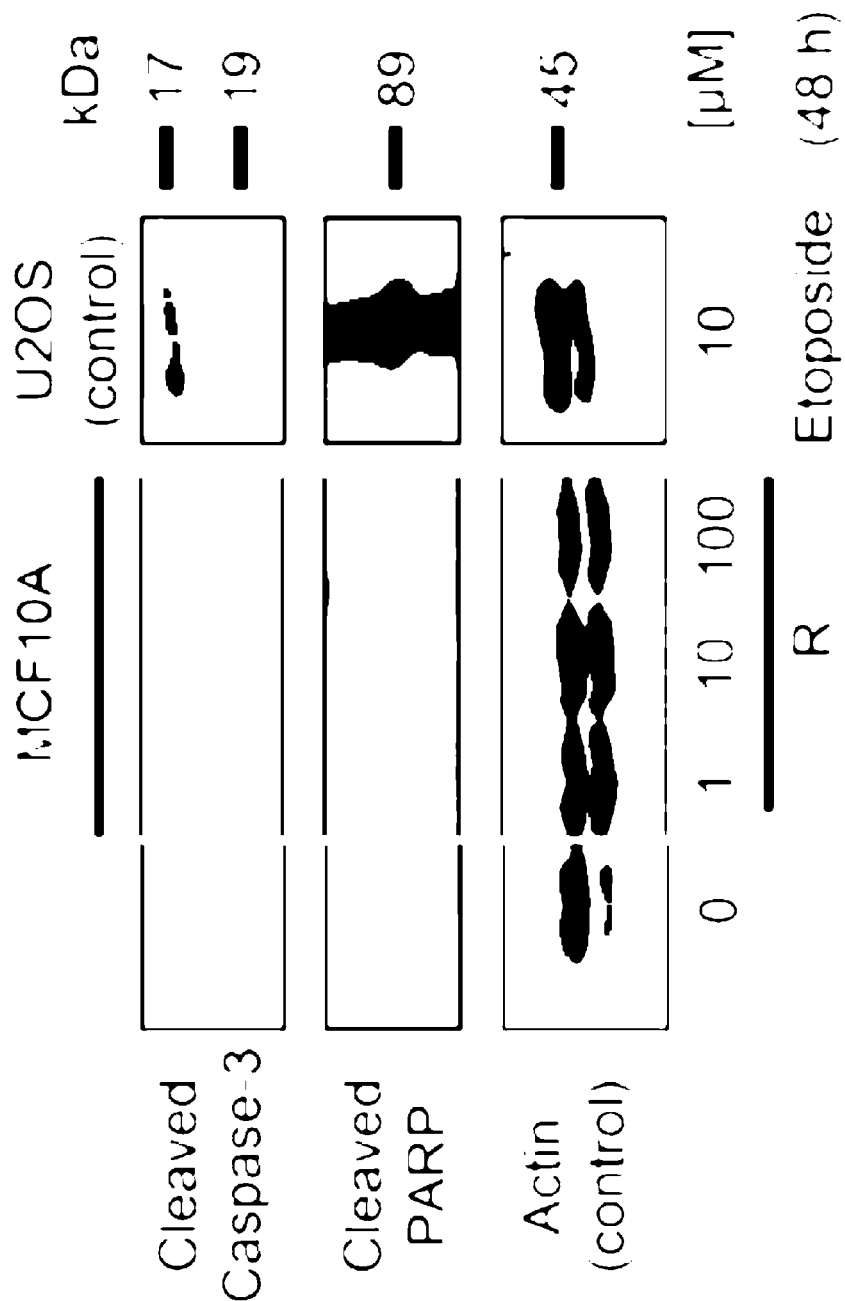

HIGH EFFICIENCY FLUORESCENT COMPOUND AND METHOD FOR PREPARING THE SAME

TECHNICAL FIELD

The present invention relates to a new fluorescent compound having high efficiency, a method for preparing the same, and its use.

BACKGROUND ART

There are cases where light is emitted from a substance at a low temperature at which the substance can not emit any visible ray by thermal radiation. Such lighting phenomenon is referred to as luminescence. Luminescence means the emission of light having a wavelength which correspond to the energy difference when a substance is converted to a stable state having low energy from an unstable state having high energy. Thus, in order to make a substance emit such light, it is necessary to make the substance to an unstable excited state having high energy. Various sources of energy such as light, chemical reactions, heat, electricity, cathode-emitted electron or the like may be used. Said difference sources of energy produce different types of light emission such as photo-, chemi-, thermo-, electro-, cathodo-luminescence, or the like.

Luminescence can be classified as fluorescence and phosphorescence. Fluorescence refers to the phenomenon that a substance emits light only when the substance is irradiated, and phosphorescence refers to the phenomenon that a substance continuously emits a light even after the irradiation to the substance is ended.

In this regard, a substance emitting fluorescence is referred to as a fluorescent element or a fluorescent substance. Such fluorescent substance can be divided into a single-photon absorption fluorescent substance which absorbs only one photon under a strong laser to emit the fluorescence and a multi-photon absorption fluorescent substance which absorbs a plurality of photons to emit the fluorescence. The present invention relates to a new fluorescent compound simultaneously having a single-photon absorption fluorescent feature as well as a multi-photon absorption fluorescent feature, in particular, 2-photon absorption fluorescent feature.

In more particular, the present invention was completed by finding a new fluorescent compound of (E)-4-(6,8-dihydroxynaphthalen-2-yl)but-3-en-2-one (hereinafter, referred to as resveratrone) having a high single-photon absorptive efficiency and/or 2-photon absorptive efficiency after a photochemical reaction of a conventionally known resveratrol which is frequently found in peanuts, grapes, berries and the like.

DISCLOSURE OF INVENTION

Technical Problem

The purpose of the present invention is to provide a new fluorescent compound with high efficiency having single-photon absorptive characteristics and/or two-photon absorptive characteristics.

Also, the purpose of the present invention is to provide a method of preparing the above fluorescent compound.

In addition, the purpose of the present invention is to provide the use of the fluorescent compound having single-photon absorptive characteristics and/or two-photon absorptive characteristics.

Solution to Problem

In order to achieve the above purposes, the present invention provides resveratrone [(E)-4-(6,8-dihydroxynaphthalen-2-yl)but-3-en-2-one] and its derivatives as a new fluorescent compound and a method for preparing the same by a photochemical reaction of resveratrol and its derivatives which are not fluorescent.

(1) A fluorescent compound represented by the following formula 1:

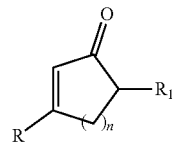

[Formula 1]

[wherein, R is naphthyl group

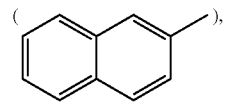

anthracenyl group

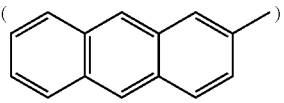

or phenalenyl group,

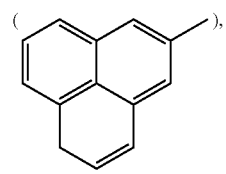

wherein said naphthyl, anthracenyl or phenalenyl group can be each independently substituted with at least one substituent selected from the group consisting of hydroxy; halogen; straight-chain or branched $C_1$-$C_{10}$ alkyl; $C_3$-$C_6$ cycloalkyl; straight-chain or branched $C_1$-$C_6$ alkoxy; $C_2$-$C_6$ heterocycloalkyl comprising N, O and/or S as heteroatom; phenyl group which is unsubstituted or substituted with at least one substituent selected from the group consisting of halogen atom, amino group, nitrile group, nitro group, $C_1$-$C_{10}$ alkyl group, $C_2$-$C_{10}$ alkenyl group, $C_1$-$C_{10}$ alkoxy group, $C_3$-$C_6$ cyclaoalkyl group, $C_2$-$C_6$ heterocycloalkyl group comprising N, O or S as heteroatom, $C_6$-$C_{16}$ aryl group, and $C_5$-$C_{15}$ heteroaryl group comprising N, O and/or S as heteroatom; benzyl group which is unsubstituted or substituted with at least one substituent selected from the group consisting of halogen atom, amino group, nitrile group, nitro group, $C_1$-$C_{10}$ alkyl group, $C_2$-$C_{10}$ alkenyl group, $C_1$-$C_{10}$ alkoxy group, $C_3$-$C_6$ cyclaoalkyl group, $C_2$-$C_6$ heterocycloalkyl group comprising N, O and/or S as heteroatom, $C_6$-$C_{30}$ aryl group and $C_5$-$C_{30}$ heteroaryl group comprising N, O and/or S as heteroatom; benzoyl; $C_1$-$C_{10}$ alkylamino; di($C_1$-$C_{10}$ alkyl)amino; and $C_1$-$C_{10}$ alkoxy;

each of $R_1$ is independently hydrogen atom; halogen, straight-chain or branched $C_1$-$C_6$ alkyl, $C_3$-$C_6$ cycloalkyl, straight-chain or branched $C_1$-$C_6$ alkoxy; $C_2$-$C_6$ heterocycloalkyl comprising N, O and/or S as heteroatom; phenyl group which is unsubstituted or substituted with at least one substituent selected from the group consisting of halogen atom, amino group, nitrile group, nitro group, $C_1$-$C_{10}$ alkyl group, $C_2$-$C_{10}$ alkenyl group, $C_1$-$C_{10}$ alkoxy group, $C_3$-$C_6$ cyclaoalkyl group, $C_2$-$C_6$ heterocycloalkyl group comprising N, O or S as heteroatom, $C_6$-$C_{16}$ aryl group, and $C_5$-$C_{15}$ heteroaryl group comprising N, O and/or S as heteroatom;

n is 0, 1, 2 or 3 (wherein, n=0 means that the carbon ring is open)].

(2) A method of preparing a fluorescent compound represented by the following Formula 1, characterized in that it comprises a step of dissolving a compound represented by Formula 7, a compound represented by Formula 8 or a mixture thereof in water or an organic solvent, and a step of subjecting to an UV irradiation:

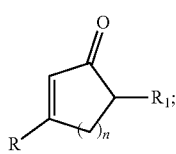

[Formula 1]

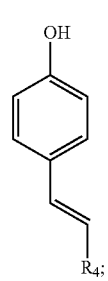

[Formula 7]

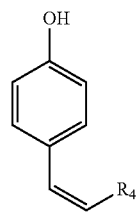

[Formula 8]

[wherein, $R_1$ and n are the same as defined in above (1), $R_4$ is substituted or unsubstituted phenyl group

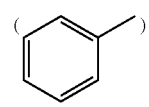

or substituted or unsubstituted naphthyl group

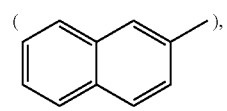

wherein, said phenyl or naphthyl group can be each independently substituted with at least one substituent selected from the group consisting of hydroxy; halogen; straight-chain or branched $C_1$-$C_{10}$ alkyl; $C_3$-$C_6$ cycloalkyl; straight-chain or branched $C_1$-$C_6$ alkoxy; $C_2$-$C_6$ heterocycloalkyl comprising N, O and/or S as heteroatom; phenyl group which is unsubstituted or substituted with at least one substituent selected from the group consisting of halogen atom, amino group, nitrile group, nitro group, $C_1$-$C_{10}$ alkyl group, $C_2$-$C_{10}$ alkenyl group, $C_1$-$C_{10}$ alkoxy group, $C_3$-$C_6$ cyclaoalkyl group, $C_2$-$C_6$ heterocycloalkyl group comprising N, O or S as heteroatom, $C_6$-$C_{16}$ aryl group, and $C_5$-$C_{15}$ heteroaryl group comprising N, O and/or S as heteroatom; benzyl group which is unsubstituted or substituted with at least one substituent selected from the group consisting of halogen atom, amino group, nitrile group, nitro group, $C_1$-$C_{10}$ alkyl group, $C_2$-$C_{10}$ alkenyl group, $C_1$-$C_{10}$ alkoxy group, $C_3$-$C_6$ cyclaoalkyl group, $C_2$-$C_6$ heterocycloalkyl group comprising N, O and/or S as heteroatom, $C_6$-$C_{30}$ aryl group and $C_5$-$C_{30}$ heteroaryl group comprising N, O and/or S as heteroatom; benzoyl; $C_1$-$C_{10}$ alkylamino; di($C_1$-$C_{10}$ alkyl)amino; and $C_1$-$C_{10}$ alkoxy].

(3) An organic fluorescent element comprising the fluorescent compound of (1).

(4) A display element comprising the organic fluorescent compound of (3).

(5) A spectrometer, a two-photon absorptive storing device, a laser micro processing apparatus, or a photo dynamic therapy apparatus, comprising the organic fluorescent element of (3).

Advantageous Effects of Invention

The new fluorescent compound of the present invention has single-photon absorptive characteristics and/or two-photon absorptive characteristics as well as no or little toxicity according to a cytotoxicity test.

BRIEF DESCRIPTION OF DRAWINGS

FIG. 1 is a graph showing emission spectra of the reactant compounds and the fluorescent compound finally produced of the present invention (wherein the highly fluorescent species is denoted by X).

FIG. 2 is a graph showing a single-photon emission spectrum (left) and a two-photon emission spectrum (right) of the fluorescent compound of the present invention.

FIG. 3 is graph showing a change of single-photon emission spectra of the fluorescent compound finally of the present invention.

FIG. 4 is a photograph showing two-photon emission of the fluorescent compound of the present invention.

FIG. 5 is a HPLC graph for the reaction products obtained after different durations of exposure to UV irradiation (wherein the highly fluorescent species is denoted by X).

FIG. 6 is a graph showing the comparison of the intensity versus wavelength of the fluorescent compounds which have been produced in the presence of ascorbic acid and in the absence of ascorbic acid, respectively.

FIG. 7 is a graph showing the comparison of the intensity versus wavelength of the fluorescent compounds which have been produced under $N_2$ atmosphere ($N_2$ purging) and not, respectively.

FIG. 8 is a graph showing an excitation spectrum of the reactant compound and an emission spectrum of the fluorescent compound finally produced in Example 10 of the present invention.

FIG. 9 is a graph showing an excitation spectrum of the reactant compound and an emission spectrum of the fluorescent compound finally produced in Example 11 of the present invention.

FIG. 10 is a graph showing an excitation spectrum of the reactant compound and an emission spectrum of the fluorescent compound finally produced in Example 12 of the present invention.

FIG. 11 is a graph showing an excitation spectrum of the reactant compound and an emission spectrum of the fluorescent compound finally produced in Example 13 of the present invention.

FIG. 12 is the photo images showing the result of Cytomorphology Test for a blank test (Control), a fluorescent compound of the present invention (Resveratrone) and a comparative compound (a commercial anticancer agent, Etoposide).

FIG. 13 is a graph showing the result of Blue Exclusion Test for a blank test (Control), a fluorescent compound of the present invention (Resveratrone) and a comparative compound (Etoposide).

FIG. 14 is a graph showing the result of Western Blotting Test for a blank test (Control), a fluorescent compound of the present invention (Resveratrone) and a comparative compound (Etoposide).

BEST MODE FOR CARRYING OUT THE INVENTION

Hereinafter, the present invention will be explained in more detail in the term of construction and effect.

The present invention provides a new fluorescent compound represented by the following formula 1:

[Formula 1]

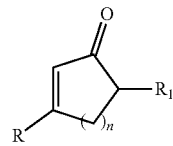

[Wherein, R is naphthyl group

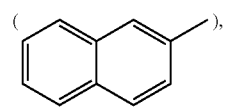

anthracenyl group

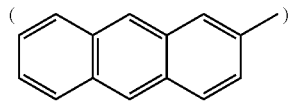

or phenalenyl group

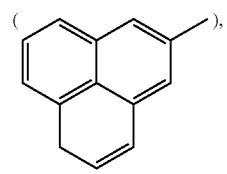

wherein said naphthyl, anthracenyl or phenalenyl group can be each independently substituted with at least one substituent selected from the group consisting of hydroxy; halogen; straight-chain or branched $C_1$-$C_{10}$ alkyl; $C_3$-$C_6$ cycloalkyl; straight-chain or branched $C_1$-$C_6$ alkoxy; $C_2$-$C_6$ heterocycloalkyl comprising N, O and/or S as heteroatom; phenyl group which is unsubstituted or substituted with at least one substituent selected from the group consisting of halogen atom, amino group, nitrile group, nitro group, $C_1$-$C_{10}$ alkyl group, $C_2$-$C_{10}$ alkenyl group, $C_1$-$C_{10}$ alkoxy group, $C_3$-$C_6$ cyclaoalkyl group, $C_2$-$C_6$ heterocycloalkyl group comprising N, O or S as heteroatom, $C_6$-$C_{16}$ aryl group, and $C_5$-$C_{15}$ heteroaryl group comprising N, O and/or S as heteroatom; benzyl group which is unsubstituted or substituted with at least one substituent selected from the group consisting of halogen atom, amino group, nitrile group, nitro group, $C_1$-$C_{10}$ alkyl group, $C_2$-$C_{10}$ alkenyl group, $C_1$-$C_{10}$ alkoxy group, $C_3$-$C_6$ cyclaoalkyl group, $C_2$-$C_6$ heterocycloalkyl group comprising N, O and/or S as heteroatom, $C_6$-$C_{30}$ aryl group and $C_5$-$C_{30}$ heteroaryl group comprising N, O and/or S as heteroatom; benzoyl; $C_1$-$C_{10}$ alkylamino; di($C_1$-$C_{10}$ alkyl)amino; and $C_1$-$C_{10}$ alkoxy; preferably, independently substituted with hydroxyl, halogen, straight-chain or branched $C_1$-$C_{10}$ alkyl, $C_3$-$C_6$ cycloalkyl, straight-chain or branched $C_1$-$C_6$ alkoxy or $C_2$-$C_6$ heterocycloalkyl comprising N, O and/or S as heteroatom; more preferably, independently substituted with hydroxyl, halogen or straight-chain or branched $C_1$-$C_{10}$ alkyl;

each of $R_1$ is independently hydrogen atom; halogen, straight-chain or branched $C_1$-$C_6$ alkyl, $C_3$-$C_6$ cycloalkyl, straight-chain or branched $C_1$-$C_6$ alkoxy; $C_2$-$C_6$ heterocycloalkyl comprising N, O and/or S as heteroatom; phenyl group which is unsubstituted or substituted with at least one substituent selected from the group consisting of halogen atom, amino group, nitrile group, nitro group, $C_1$-$C_{10}$ alkyl group, $C_2$-$C_{10}$ alkenyl group, $C_1$-$C_{10}$ alkoxy group, $C_3$-$C_6$ cyclaoalkyl group, $C_2$-$C_6$ heterocycloalkyl group comprising N, O or S as heteroatom, $C_6$-$C_{16}$ aryl group, and $C_5$-$C_{15}$ heteroaryl group comprising N, O and/or S as heteroatom; preferably, selected from the group consisting of hydrogen atom, hydroxyl, halogen, straight-chain or branched $C_1$-$C_{10}$ alkyl, $C_3$-$C_6$ cycloalkyl, straight-chain or branched $C_1$-$C_6$ alkoxy or $C_2$-$C_6$ heterocycloalkyl comprising N, O and/or S as heteroatom; more preferably, selected from the group consisting of hydrogen atom, hydroxyl, halogen or straight-chain or branched $C_1$-$C_{10}$ alkyl;

n is 0, 1, 2 or 3, preferably 0 or 1, more preferably 0 (wherein, n=0 means that the carbon ring is open)].

Also, the present invention provides a fluorescent compound represented by any one of the following formulae 2~6:

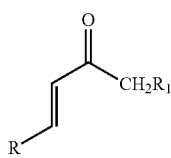

[Formula 2]

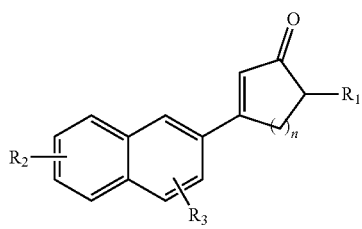

[Formula 3]

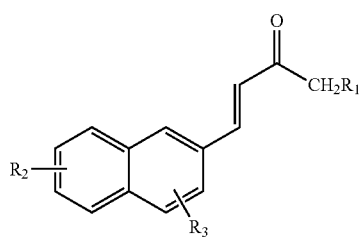

[Formula 4]

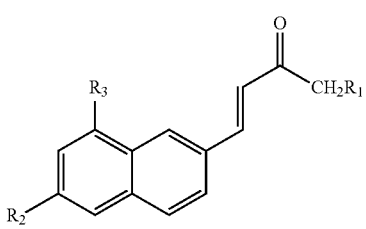

[Formula 5]

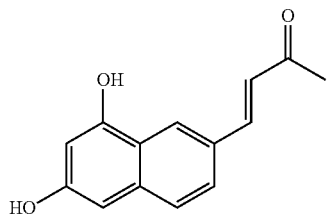

[Formula 6]

[wherein, R, $R_1$ and n are the same as defined in the above, and $R_2$ and $R_3$ are each independently selected from a group consisting of hydrogen atom; hydroxy; halogen; straight-chain or branched $C_1$-$C_{10}$ alkyl; $C_3$-$C_6$ cycloalkyl; straight-chain or branched $C_1$-$C_6$ alkoxy; $C_2$-$C_6$ heterocycloalkyl comprising N, O and/or S as heteroatom; phenyl group which is unsubstituted or substituted with at least one substituent selected from the group consisting of halogen atom, amino group, nitrile group, nitro group, $C_1$-$C_{10}$ alkyl group, $C_2$-$C_{10}$ alkenyl group, $C_1$-$C_{10}$ alkoxy group, $C_3$-$C_6$ cyclaoalkyl group, $C_2$-$C_6$ heterocycloalkyl group comprising N, O or S as heteroatom, $C_6$-$C_{16}$ aryl group, and $C_5$-$C_{15}$ heteroaryl group comprising N, O and/or S as heteroatom; benzyl group which is unsubstituted or substituted with at least one substituent selected from the group consisting of halogen atom, amino group, nitrile group, nitro group, $C_1$-$C_{10}$ alkyl group, $C_2$-$C_{10}$ alkenyl group, $C_1$-$C_{10}$ alkoxy group, $C_3$-$C_6$ cyclaoalkyl group, $C_2$-$C_6$ heterocycloalkyl group comprising N, O and/or S as heteroatom, $C_6$-$C_{30}$ aryl group and $C_5$-$C_{30}$ heteroaryl group comprising N, O and/or S as heteroatom; benzoyl; $C_1$-$C_{10}$ alkylamino; di($C_1$-$C_{10}$ alkyl)amino; and $C_1$-$C_{10}$ alkoxy; preferably, independently selected from the group consisting of hydrogen atom, hydroxyl, halogen, straight-chain or branched $C_1$-$C_{10}$ alkyl, $C_3$-$C_6$ cycloalkyl, straight-chain or branched $C_1$-$C_6$ alkoxy or $C_2$-$C_6$ heterocycloalkyl comprising N, O and/or S as heteroatom; more preferably, independently selected from the group consisting of hydrogen atom, hydroxyl, halogen or straight-chain or branched $C_1$-$C_{10}$ alkyl.]

Also, the present invention provides a method of preparing a fluorescent compound represented by formula 1 above.

In particular, a fluorescent compound represented by formula 1 above is prepared via a method comprises a step of dissolving a compound represented by the following Formula 7, a compound represented by the following Formula 8 or a mixture thereof in water, an organic solvent or mixture thereof and a step of subjecting to a UV irradiation:

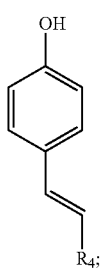

[Formula 7]

-continued

[Formula 8]

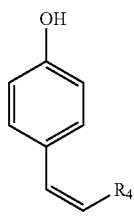

[wherein, $R_1$ and n are the same as defined as above, $R_4$ is substituted or unsubstituted phenyl group

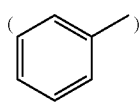

or substituted or unsubstituted naphthyl group

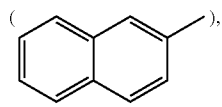

wherein, said phenyl or naphthyl group can be each independently substituted with at least one substituent selected from the group consisting of hydroxy; halogen; straight-chain or branched $C_1$-$C_{10}$ alkyl; $C_3$-$C_6$ cycloalkyl; straight-chain or branched $C_1$-$C_6$ alkoxy; $C_2$-$C_6$ heterocycloalkyl comprising N, O and/or S as heteroatom; phenyl group which is unsubstituted or substituted with at least one substituent selected from the group consisting of halogen atom, amino group, nitrile group, nitro group, $C_1$-$C_{10}$ alkyl group, $C_2$-$C_{10}$ alkenyl group, $C_1$-$C_{10}$ alkoxy group, $C_3$-$C_6$ cyclaoalkyl group, $C_2$-$C_6$ heterocycloalkyl group comprising N, O or S as heteroatom, $C_6$-$C_{16}$ aryl group, and $C_5$-$C_{15}$ heteroaryl group comprising N, O and/or S as heteroatom; benzyl group which is unsubstituted or substituted with at least one substituent selected from the group consisting of halogen atom, amino group, nitrile group, nitro group, $C_1$-$C_{10}$ alkyl group, $C_2$-$C_{10}$ alkenyl group, $C_1$-$C_{10}$ alkoxy group, $C_3$-$C_6$ cyclaoalkyl group, $C_2$-$C_6$ heterocycloalkyl group comprising N, O and/or S as heteroatom, $C_6$-$C_{30}$ aryl group and $C_5$-$C_{30}$ heteroaryl group comprising N, O and/or S as heteroatom; benzoyl; $C_1$-$C_{10}$ alkylamino; di($C_1$-$C_{10}$ alkyl)amino; and $C_1$-$C_{10}$ alkoxy; preferably, independently substituted with hydroxyl, halogen, straight-chain or branched $C_1$-$C_{10}$ alkyl, $C_3$-$C_6$ cycloalkyl, straight-chain or branched $C_1$-$C_6$ alkoxy or $C_2$-$C_6$ heterocycloalkyl comprising N, O and/or S as heteroatom; more preferably, independently substituted with hydroxyl, halogen or straight-chain or branched $C_1$-$C_{10}$ alkyl.]

A method of preparing (E)-4-(6,8-dihydroxynaphthalen-2-yl)but-3-en-2-one (resveratrone) corresponding to the above Formula 1 by photochemical reaction of trans- and/or cis-resveratrol corresponding to the above Formula 7 can be exemplified by the following reaction formula 1.

[Reaction Formula 1]

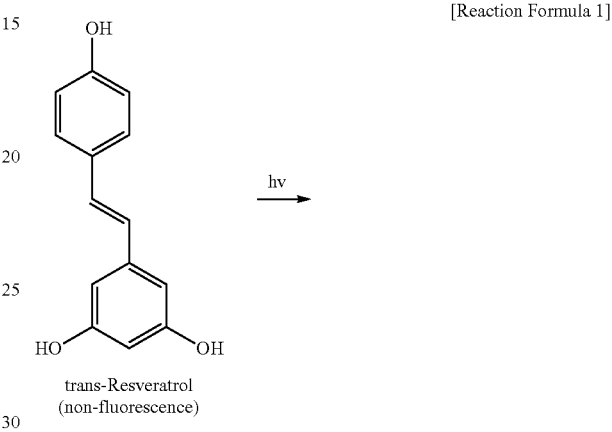

trans-Resveratrol
(non-fluorescence)

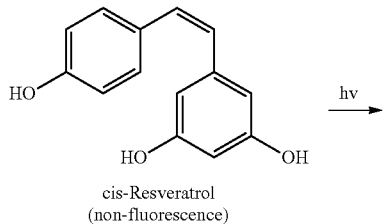

cis-Resveratrol
(non-fluorescence)

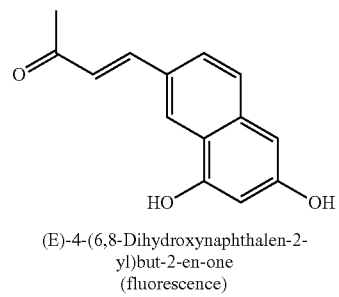

(E)-4-(6,8-Dihydroxynaphthalen-2-yl)but-2-en-one
(fluorescence)

Also, the above Reaction formula 1 can be schematized as follows:

[Reaction Formula 2]

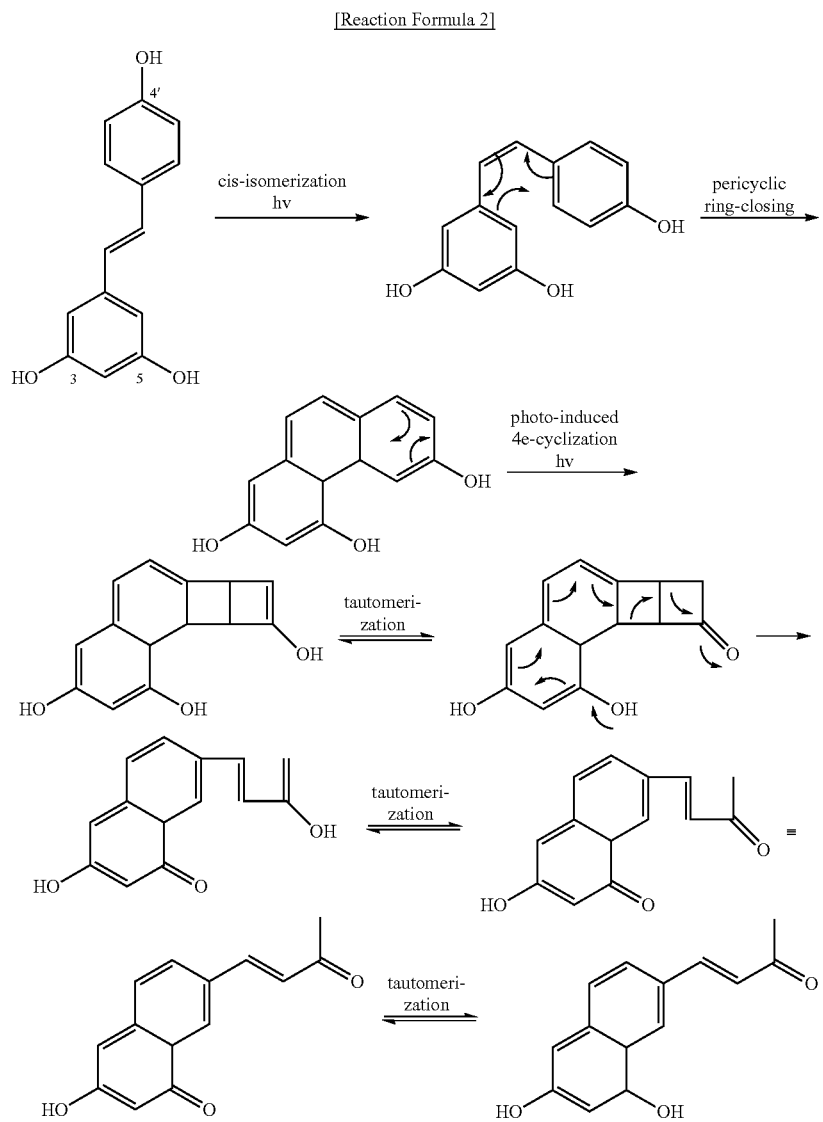

As to the organic solvent which can be used in the present invention, it is possible to mention protic solvents such as ethanol, methanol, n-propanol, iso-propanol, n-butanol, DMSO (dimethyl sulfoxide), EA (ethyl ester), THF (tetrahydrofuran) and the like, which can be used alone or as a mixture thereof. Ethanol, methanol, n-propanol, iso-propanol, n-butanol or DMSO are preferable, and DMSO is most preferable.

According to a preferred embodiment of the present invention, in order to improve the yield of the product, the reaction mixture can additionally include an antioxidant such as, for example, ascorbic acid, polyphenols, glutathione, N-acetylcystein, -tocopherol, butylated hydroxyanisole (BHA), catechin, quercetin, uric acid, bilirubin, glucose, flavonoid or the like, which can be added alone or as mixture thereof, after dissolving a compound represented by Formula 7, a compound represented by Formula 8 or a mixture thereof in water or an organic solvent, and before subjecting to an UV irradiation. Among them, ascorbic acid or polyphenol is preferable.

According to a preferred embodiment of the present invention, in order to improve the yield of the product, the reaction can be conducted under $N_2$ atmosphere ($N_2$ purging).

The reaction temperature at the photochemical reaction can be selected from $-10\sim100°$ C., particularly 0 and $60°$ C., preferably between 10 and $40°$ C., and more preferably between 20 and $30°$ C. The wavelength of UV ray to be irradiated can be selected from 100~500 nm, preferably 200~400 nm, and more preferably 250~450 nm. The irradiation time can be selected from 5 second~50 minutes, particularly 6 second~40 minutes, preferably 8 seconds~30 minutes, and more preferably 10 seconds~20 minutes. In addition, the reaction temperature, UV wavelength and irradiation time is not strictly limited to the above ranges and can be easily modified according to the purpose.

The fluorescent compound of the present invention prepared by the above method has high efficiency single-photon absorptive characteristics and/or two-photon absorptive characteristics (see FIGS. 2~4). Thus, the fluorescent compound of the present invention can be utilized in an organic fluorescent element including a fluorescent compound as well as in a display element including an organic fluorescent elements. The display element can be a plasma display panel, a cathode-ray tube (CRT), a lamp, or the like.

Further, the fluorescent compound according to the present invention does not have toxicity to a cell which can be verified by a cytotoxicity test (see FIGS. 12~14 and Test Examples 1~3). Thus, it can be used as an organic fluorescent element directed to a specific target in cells.

In addition, the fluorescent compound according to the present invention can be usefully utilized in the field of a spectrometer, a two-photon absorptive storing device, a laser micro processing apparatus, a photo dynamic therapy apparatus or the like.

Hereinafter, the present invention is explained in more detail with reference to the examples. However, the following examples are merely to exemplify the present invention and the present invention is not limited to the following examples and various corrections and modifications can be made.

MODE FOR THE INVENTION

Examples

In General $^1$H NMR and $^{13}$C NMR spectra are recorded on Bruker Avance 600 (Bruker Biospin, Germany) and Varian Inova-500 (Varian Assoc., Palo Alto, USA), wherein data are reported in the following order: chemical shift (δ) in ppm; multiplicities are indicated bs (broadened singlet), s (singlet), d (doublet), m (multiplet), dd (doublet of doubled); coupling constants (J) are in Hertz (Hz).

Identification of the desired fluorescent compound is confirmed by high-resolution mass spectrometry (HRMS; LTQ orbitrab). HRMS analysis is conducted using a High-Resolution Liquid Chromatography/Tandem Mass Analysis equipment located at the National Instrumentation Center for Environmental Management of Seoul National University.

UV absorption of the final fluorescent compound is determined by using a UV-VISIBLE spectrophotometer (Perkin Elmer, USA). Maximum values of excitation and emission are determined by using a fluorescent spectrophotometer (PTI, USA).

The absolute quantum yield is determined by using an absolute PL quantum yield measurement system (QE-1000, Otsuka Electronics, Japan). The relative quantum yield is determined by measuring the absorbance and emission intensity for each five concentrations for one solvent, determining the slope of said measured values, and comparing the slope with that of rhodamin 6G (the quantum yield of rhodamin 6G in ethanol is 0.95).

trans-Resveratrol and trans-pterostilbene are commercially available (from sigma-Aldlich and TCI, respectively). Other solvents and organic samples are purchased in the market and used without any additional purification unless there is any other description. Distilled water is completed by ion exchange and filtration.

Preparation of the Fluorescent Compound of the Present Invention

Example 1: Preparation of (E)-4-(6,8-dihydroxynaphthalen-2-yl)but-3-en-2-one

A solution of trans-resveratrone (R5010, sigma-Aldlich; 125 M) in 300 mL of methanol is subjected to a UV irradiation at 295 K for 90 seconds by using a UV lamp (λmax=305 nm) of 6-watt to give the titled compound of the following Formula 6.

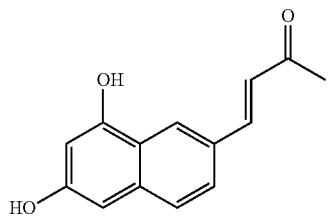

[Formula 6]

$^1$H NMR (600 MHz, MeOD) δ: 8.21 (s, 1H), 7.69 (d, J=16.2 Hz, 1H), 7.56 (dd, J=8.7, 1.1 Hz, 1H), 7.50 (d, J=8.7 Hz, 1H), 6.71 (d, J=16.2 Hz, 1H), 6.63 (d, J=1.7 Hz, 1H), 6.50 (d, J=1.9 Hz, 1H), 2.35 (s, 3H); $^{13}$C NMR (125 MHz, MeOD) 201.6, 159.1, 156.9, 147.1 138.6, 128.9, 127.8, 127.1, 125.5, 125.1, 121.2, 102.1, 27.1; HRMS (ESI): m/z calcd for $C_{14}H_{11}O_3[M]^-$ 227.0714, found 227.0742.

Examples 2~6

Except for conducting the photochemical reaction in the presence of an organic solvent such as ethanol (Example 2), n-propanol (Example 3), iso-propanol (Example 4), n-butanol (Example 5) or DMSO (Example 6), respectively, the fluorescent compound is obtained from trans-resveratrol in the same manner as Example 1. Quantum yields of each organic solvent are shown in Table 1.

TABLE 1

| | Solvent | Excitation(nm) | Emission(nm) | Relative quantum yield | Absolute quantum yield |
|---|---|---|---|---|---|
| Example 1 | Methanol | 390 | 547 | 0.035 | 0.058 |
| Example 2 | Ethanol | 390 | 540 | 0.103 | 0.145 |
| Example 3 | n-Propanol | 390 | 534 | 0.155 | 0.212 |
| Example 4 | iso-Propanol | 390 | 525 | 0.247 | 0.311 |
| Example 5 | n-Butanol | 390 | 536 | 0.200 | 0.254 |
| Example 6 | DMSO | 390 | 497 | 0.523 | 0.439 |

Example 7

Except for using trans-pterostilbene as the reactant compound, the fluorescent compound is obtained from trans-resveratrol in the same manner as Example 1.

The emission spectra of the obtained compound is shown in FIG. 3, wherein the time of 0 min, 2 min and 4 min means the UV irradiation, thus the spectrum at 0 min is for the reactant (trans-pterostilbene). As can be seen in FIG. 3, it can be confirmed that the final compound prepared from a non-fluorescent compound of trans-pterostilbene is a fluorescent compound.

Example 8

Except for additionally adding ascorbic acid (50 μM, 40 μL) to a solution (125 μM) of trans-resveratrone (R5010, sigma-Aldlich; 8.559 mg) in 300 mL of methanol before subjecting to an UV irradiation, the fluorescent compound is obtained from trans-resveratrol in the same manner as Example 1.

FIG. 6 shows each graph of intensity versus wavelength of the final product obtained with adding ascorbic acid and the final product obtained without adding ascorbic acid. As can be seen in FIG. 6, it can be understood that the intensity of the final product obtained with adding ascorbic acid is higher than that obtained without adding ascorbic acid.

Example 9

Except for conducting the photochemical reaction under $N_2$ atmosphere or with $N_2$ purging), the fluorescent compound is obtained from trans-resveratrol in the same manner as Example 1.

FIG. 7 shows each graph of intensity versus wavelength of the final product obtained with conducting under $N_2$ atmosphere and the final product obtained without conducting under $N_2$ atmosphere. As can be seen in FIG. 7, it can be understood that the intensity of the final product obtained with conducting under $N_2$ atmosphere is higher than that obtained without conducting under $N_2$ atmosphere.

Example 10: Preparation of (Z)-4-(6,8-dihydroxynaphthalen-2-yl)-4-hydroxybut-3-en-2-one A solution of oxyresveratrol (9.159 mg) [O0373, SejinCI Company; 2,3',4,5'-Tetrahydroxy-trans-stilbene] in 300 mL of methanol is subjected to a UV irradiation at 295 K for 2 minutes by using a UV lamp (λmax=305 nm) of 6-watt to give the titled compound represented by following Formula 9. The excitation spectrum of the reactant compound and the emission spectrum of the final fluorescent compound are shown in FIG. 8.

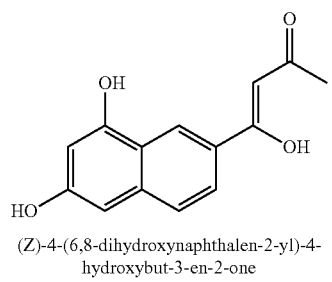

[Formula 9]

(Z)-4-(6,8-dihydroxynaphthalen-2-yl)-4-hydroxybut-3-en-2-one

Example 11: Preparation of (E)-4-(5,7-dimethoxynaphthalen-3-yl)but-3-en-2-one

A solution of pterostilbene (9.611 mg) [P1928, SejinCI Company; trans-1-(3,5-Dimethoxyphenyl)-2-(4-hydroxyphenyl)ethylene] in 300 mL of methanol is subjected to a UV irradiation at 295 K for 5 minutes 30 seconds by using a UV lamp (λmax=305 nm) of 6-watt to give the titled compound represented by following Formula 10. The excitation spectrum of the reactant compound and the emission spectrum of the final fluorescent compound are shown in FIG. 9.

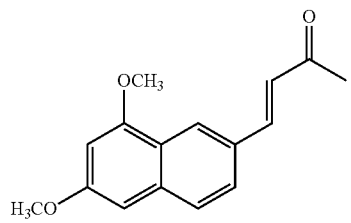

[Formula 10]

Example 12: Preparation of (E)-4-(6,8-dihydroxynaphthalen-2-yl)methoxybut-3-en-2-one A solution of isorhapontigenin (9.685 mg) [I0804, SejinCI Company; 3,4',5-Trihydroxy-3'-methoxy-trans-stilbene] in 300 mL of methanol is subjected to a UV irradiation at 295 K for 7 minutes by using a UV lamp (λmax=305 nm) of 6-watt to give the titled compound represented by following Formula 11. The excitation spectrum of the reactant compound and the emission spectrum of the final fluorescent compound are shown in FIG. 10.

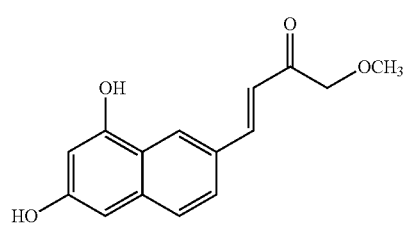

[Formula 11]

Example 13: Preparation of (E)-4-(8-hydroxy-6-methoxynaphthalen-2-yl)but-3-en-2-one A solution of pinostilbene hydrate (9.085 mg) (SML0098, sigma-Aldlich; 3,4'-Dihydroxy-5-methoxy-trans-stilbene) in 300 mL of methanol is subjected to a UV irradiation at 295 K for 4 minutes 30 seconds by using a UV lamp (λmax=305 nm) of 6-watt to give the titled compound represented by following Formula 12. The excitation spectrum of the reactant compound and the emission spectrum of the final fluorescent compound are shown in FIG. 11.

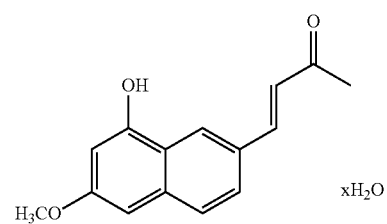

[Formula 12]

Test Example: Cytotoxicity Test

In the presence of a test compound or a comparative compound, a cell line is cultured for a certain period of time (about 72 hours) and then a cytotoxicity test is conducted. As a control group, a blank test is conducted in the same manner as above without adding any compound including the test compound and the comparative compound.

Test Example 1: Cytomorphology Test

A breast epithelial cell line cultured in the presence of a test compound (Resveratrone, the fluorescent compound obtained in Example 1) and a comparative compound (Etoposide, a commercial anticancer agent), respectively, and a microscopic examination is conducted to evaluate the cytomorphology and number change of the cultured cell.

FIG. 12 shows each microscopic photo image of the resulting breast epithelial cells after cultured in a blank test (control group, left) and in the presence of the test fluorescent compound (Resveratrone, center) or the comparative compound (Etoposide, right), respectively. In FIG. 12, it can be confirmed that the comparative compound (Etoposide) results to a remarkable reduction in the number of cells in comparison with the control group, while the test compound (Resveratrone) has no significant difference from the control group.

Therefore, it can be understood from FIG. 12 that the test compound (Resveratrone) of the present invention has no or little cell toxicity and very high stability in comparison with the commercial anticancer agent (Etoposide).

Test Example 2: Trypan Blue Exclusion Test

To the each resulting breast epithelial cell cultured and microscopically examined in Test Example 1, a trypan blue test solution which does not dye cells alive is added and the number of cells alive is counted to evaluate the cell toxicity of the test compound and the comparative compound by comparing with the control group.

FIG. 13 is a graph showing the result of Blue Exclusion Test for the control group (blank), the test compound (resveratrone) and the comparative compound (etoposide), respectively. In FIG. 13, the test compound (left side) results to a number of cells similar to that of the control group in both test concentrations (1 μM and 10 μM), while the comparative compound (right side) results to a remarkably reduced number of cells in both test concentrations (1 μM and 10 μM).

Therefore, it can be understood from FIG. 13 that the test compound (Resveratrone) of the present invention has no or little cell toxicity and a very high stability in comparison with the commercial anticancer agent (Etoposide).

Test Example 3. Western Blotting Test

A breast epithelial cell line is cultured in a blank test (control group) and in the presence of a test compound (Resveratrone), respectively, and an osteosarcoma cell line (U2OS) is cultured in the presence of a comparative compound (Etoposide).

After a certain period of time, the degree of cell extinction is evaluated by examining the degree of expression of extinction and damage of a specific factor by using Western Blotting Test and the result is shown in FIG. 14.

In FIG. 14, the blank test (left side, Control group, concentration of 0 μM) and the test compound (center side, Resveratrone, three concentrations of 1, 10 and 100 μM) show only a peak at 45 kDa position and no peak at 17 kDa, 19 kDa and 89 kDa positions which result from cell extinction and damage. Therefore, it can be understood that the test compound does not give any significant level of cell extinction and damage.

Further, the comparative compound (right side, Etoposide, concentration of 10 μM) shows a significantly remarkable peak at 17 kDa, 19 kDa and 89 kDa positions which result from cell extinction and damage, by which it can be understood that a lot of cells are extinguished and/or damaged.

As a result, it can be understood from FIG. 14 that the test compound (Resveratrone) of the present invention has no or little cell toxicity.

The terms used in FIG. 14 have the following meanings:
Caspase-3: one of proteins found when cells die
PARP: one of proteins found when cells die
Actin: a procedure for confirming whether the current Western Blotting System is normally operating (control group)
Osteosarcoma cells (U2OS): one of cancer cell lines
Etoposide: one of commercial anticancer agents In the result using osteosarcoma cells (U2OS) in the presence of a comparative compound (etoposide), the expression of the above specific proteins means that the Western Blotting System is normally operating.

INDUSTRIAL APPLICABILITY

The new fluorescent compound of the present invention can be usefully utilized in the field of organic fluorescent element, display element, spectrometer, two-photon absorptive storing device, laser micro processing apparatus, photo dynamic therapy apparatus and the like.

The invention claimed is:

1. A fluorescent compound represented by the following formula 2:

[Formula 2]

$$\underset{R}{\overset{O}{\underset{\|}{C}}}\text{—}CH_2R_1$$

wherein R is naphthyl group (naphthyl structure), anthracenyl group (anthracenyl structure)

or phenalenyl group (phenalenyl structure);

wherein said naphthyl, anthracenyl or phenalenyl group are each independently substituted with at least two substituents selected from the group consisting of hydroxy; halogen; straight-chain or branched $C_1$-$C_{10}$ alkyl; $C_3$-$C_6$ cycloalkyl; straight-chain or branched $C_1$-$C_6$ alkoxy; $C_2$-$C_6$ heterocycloalkyl comprising N, O and/or S as heteroatom; phenyl group which is unsubstituted or substituted with at least one substituent selected from the group consisting of halogen atom, amino group, nitrile group, nitro group, $C_1$-$C_{10}$ alkyl group, $C_2$-$C_{10}$ alkenyl group, $C_1$-$C_{10}$ alkoxy group, $C_3$-$C_6$ cyclaoalkyl group, $C_2$-$C_6$ heterocycloalkyl group comprising N, O or S as heteroatom, $C_6$-$C_{16}$ aryl group, and $C_5$-$C_{15}$ heteroaryl group comprising N, O and/or S as heteroatom; benzyl group which is unsubstituted or substituted with at least one substituent selected from the group consisting of halogen atom, amino group, nitrile group, nitro group, $C_1$-$C_{10}$ alkyl group, $C_2$-$C_{10}$ alkenyl group, $C_1$-$C_{10}$ alkoxy group, $C_3$-$C_6$ cyclaoalkyl group, $C_2$-$C_6$ heterocycloalkyl group comprising N, O and/or S as heteroatom, $C_6$-$C_{30}$ aryl group and $C_5$-$C_{30}$ heteroaryl group comprising N, O and/or S as heteroatom; benzoyl; $C_1$-$C_{10}$ alkylamino; di($C_1$-$C_{10}$ alkyl)amino; and $C_1$-$C_{10}$ alkoxy; and wherein $R_1$ is selected from the group consisting of hydrogen atom; halogen, straight-chain or branched $C_1$-$C_6$ alkyl, $C_3$-$C_6$ cycloalkyl, straight-chain or branched $C_1$-$C_6$ alkoxy; $C_2$-$C_6$ heterocycloalkyl comprising N, O and/or S as heteroatom; and phenyl group which is unsubstituted or substituted with at least one substituent selected from the group consisting of halogen atom, amino group, nitrile group, nitro group, $C_1$-$C_{10}$ alkyl group, $C_2$-$C_{10}$ alkenyl group, $C_1$-$C_{10}$ alkoxy group, $C_3$-$C_6$ cyclaoalkyl group, $C_2$-$C_6$ heterocycloalkyl group comprising N, O or S as heteroatom, $C_6$-$C_{16}$ aryl group, and $C_5$-$C_{15}$ heteroaryl group comprising N, O and/or S as heteroatom.

2. The fluorescent compound according to claim 1, wherein the compound is represented by the following formula 4:

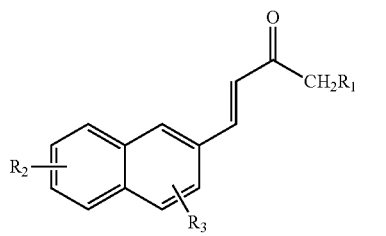

[Formula 4]

wherein $R_1$ is the same as defined in claim 1, and
wherein $R_2$ and $R_3$ are each independently selected from a group consisting of hydrogen atom; hydroxy; halogen; straight-chain or branched $C_1$-$C_{10}$ alkyl; $C_3$-$C_6$ cycloalkyl; straight-chain or branched $C_1$-$C_6$ alkoxy; $C_2$-$C_6$ heterocycloalkyl comprising N, O and/or S as heteroatom; phenyl group which is unsubstituted or substituted with at least one substituent selected from the group consisting of halogen atom, amino group, nitrile group, nitro group, $C_1$-$C_{10}$ alkyl group, $C_2$-$C_{10}$ alkenyl group, $C_1$-$C_{10}$ alkoxy group, $C_3$-$C_6$ cyclaoalkyl group, $C_2$-$C_6$ heterocycloalkyl group comprising N, O or S as heteroatom, $C_6$-$C_{16}$ aryl group, and $C_5$-$C_{15}$ heteroaryl group comprising N, O and/or S as heteroatom; benzyl group which is unsubstituted or substituted with at least one substituent selected from the group consisting of halogen atom, amino group, nitrile group, nitro group, $C_1$-$C_{10}$ alkyl group, $C_2$-$C_{10}$ alkenyl group, $C_1$-$C_{10}$ alkoxy group, $C_3$-$C_6$ cyclaoalkyl group, $C_2$-$C_6$ heterocycloalkyl group comprising N, O and/or S as heteroatom, $C_6$-$C_{30}$ aryl group and $C_5$-$C_{30}$ heteroaryl group comprising N, O and/or S as heteroatom; benzoyl; $C_1$-$C_{10}$ alkylamino; di($C_1$-$C_{10}$ alkyl)amino; and $C_1$-$C_{10}$ alkoxy.

3. The fluorescent compound according to claim 2, wherein the compound is represented by the following formula 5:

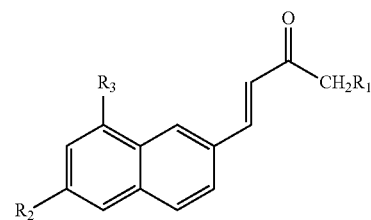

[Formula 5]

wherein, $R_1$, $R_2$ and $R_3$ are the same as defined in claim 2.

4. The fluorescent compound according to claim 3, wherein the compound is represented by the following formula 6:

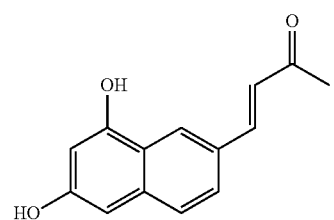

[Formula 6]

5. A method of preparing a fluorescent compound represented by the following Formula 1, the method comprising dissolving a compound represented by Formula 7, a compound represented by Formula 8 or a mixture thereof in water or an organic solvent, and subjecting to an UV irradiation:

[Formula 1]

-continued

[Formula 7]

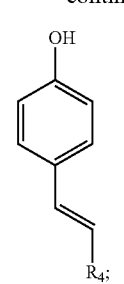

[Formula 8]

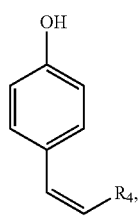

wherein, $R_1$ and n are the same as defined in claim 1, and $R_4$ is substituted or unsubstituted phenyl group

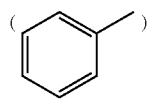

or substituted or unsubstituted naphthyl group

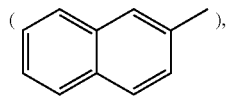

wherein, said phenyl or naphthyl group can be each independently substituted with at least one substituent selected from the group consisting of hydroxy; halogen; straight-chain or branched $C_1$-$C_{10}$ alkyl; $C_3$-$C_6$ cycloalkyl; straight-chain or branched $C_1$-$C_6$ alkoxy; $C_2$-$C_6$ heterocycloalkyl comprising N, O and/or S as heteroatom; phenyl group which is unsubstituted or substituted with at least one substituent selected from the group consisting of halogen atom, amino group, nitrile group, nitro group, $C_1$-$C_{10}$ alkyl group, $C_2$-$C_{10}$ alkenyl group, $C_1$-$C_{10}$ alkoxy group, $C_3$-$C_6$ cyclaoalkyl group, $C_2$-$C_6$ heterocycloalkyl group comprising N, O or S as heteroatom, $C_6$-$C_{16}$ aryl group, and $C_5$-$C_{15}$ heteroaryl group comprising N, O and/or S as heteroatom; benzyl group which is unsubstituted or substituted with at least one substituent selected from the group consisting of halogen atom, amino group, nitrile group, nitro group, $C_1$-$C_{10}$ alkyl group, $C_2$-$C_{10}$ alkenyl group, $C_1$-$C_{10}$ alkoxy group, $C_3$-$C_6$ cyclaoalkyl group, $C_2$-$C_6$ heterocycloalkyl group comprising N, O and/or S as heteroatom, $C_6$-$C_{30}$ aryl group and $C_5$-$C_{30}$ heteroaryl group comprising N, O and/or S as heteroatom; benzoyl; $C_1$-$C_{10}$ alkylamino; di($C_1$-$C_{10}$ alkyl)amino; and $C_1$-$C_{10}$ alkoxy.

6. The method according to claim 5, further comprising adding ascorbic acid, polyphenol or a mixture thereof after dissolving a compound represented by Formula 7, a compound represented by Formula 8 or a mixture thereof in water or an organic solvent, and before subjecting to an UV irradiation.

7. The method according to claim 5, wherein the method is conducted under $N_2$ atmosphere or $N_2$ purging.

8. An organic fluorescent element comprising fluorescent compounds according to claim 1.

9. A display element comprising organic fluorescent elements according to claim 8.

10. A spectrometer, a two-photon absorptive storing device, a laser micro processing apparatus, or a photo dynamic therapy apparatus, comprising the organic fluorescent elements according to claim 8.

11. An organic fluorescent element comprising fluorescent compounds according to claim 2.

12. An organic fluorescent element comprising fluorescent compounds according to claim 3.

13. An organic fluorescent element comprising fluorescent compounds according to claim 4.

* * * * *